(12) United States Patent
Gibbs et al.

(10) Patent No.: US 7,771,974 B2
(45) Date of Patent: Aug. 10, 2010

(54) DEGENERATE OLIGONUCLEOTIDE GENE SHUFFLING

(75) Inventors: Moreland David Gibbs, Marsfield (AU); Peter Leonard Bergquist, Chatswood (AU); Kaisu Milja Helena Nevalainen, North Epping (AU)

(73) Assignee: Macquarie University, New South Wales (AU)

( * ) Notice: Subject to any disclaimer, the term of this patent is extended or adjusted under 35 U.S.C. 154(b) by 743 days.

(21) Appl. No.: 10/362,829

(22) PCT Filed: Aug. 29, 2001

(86) PCT No.: PCT/AU01/01080

§ 371 (c)(1),
(2), (4) Date: Jul. 1, 2003

(87) PCT Pub. No.: WO02/18629

PCT Pub. Date: Mar. 7, 2002

(65) Prior Publication Data

US 2004/0053267 A1 Mar. 18, 2004

(30) Foreign Application Priority Data

Aug. 29, 2000 (AU) .................................. PQ9749

(51) Int. Cl.
*C12P 19/34* (2006.01)
*C07H 21/04* (2006.01)
(52) U.S. Cl. .................................. 435/91.2; 536/24.33
(58) Field of Classification Search .................. None
See application file for complete search history.

(56) References Cited

U.S. PATENT DOCUMENTS

| 6,222,022 B1 * | 4/2001 | Johnson et al. ............. 530/399 |
| 6,376,246 B1 * | 4/2002 | Crameri et al. ............. 435/440 |
| 6,613,514 B2 * | 9/2003 | Patten et al. .................... 435/6 |

FOREIGN PATENT DOCUMENTS

| WO | WO 98/05765 A1 | 2/1998 |
| WO | WO 98/41622 A1 | 9/1998 |
| WO | WO 98/41653 | 9/1998 |
| WO | WO 9841623 A1 * | 9/1998 |
| WO | WO 98/42728 | 10/1998 |

(Continued)

OTHER PUBLICATIONS

Hayashi et al. Simultaneous mutagenesis of antibody CDR regions by overlap extension and PCR. Biotechniques, vol. 17, No. 2, pp. 310, 312, 314-315, published 1994).*

(Continued)

*Primary Examiner*—Samuel Woolwine
(74) *Attorney, Agent, or Firm*—Cooley LLP

(57) ABSTRACT

A method for gene shuffling to form a mutant or chimeric gene, the method comprising: (a) assigning one or more segments of one or more genes based on regions of encoded amino acid sequence; (b) amplifying the one or more assigned segments of the gene using primers specific for each segment; and (c) causing recombination of the one or more amplified segments to form a mutant or chimeric gene. An oligonucleotide primer suitable for use in gene shuffling, the primer having a non-degenerate core based on a segment or template of a gene to be amplified, and the core being flanked by both 5' and 3' degenerate ends.

21 Claims, 7 Drawing Sheets

FOREIGN PATENT DOCUMENTS

WO     WO 98/58080 A1     12/1998
WO     WO 00/09727 A2     2/2000

OTHER PUBLICATIONS

Castrop et al. A gene family of HMG-box transcription factors with homology to TCF-1. Nucleic Acids Research 20(3):611 (1992).*

Rose et al. Consensus-degenerate hybrid oligonucleotide primers for amplification of distantly related sequences. Nucleic Acids Research 26(7):1628-1635 (1998).*

Crameri et al. (1998) "DNA shuffling of a family of genes from diverse species accelerates directed evolution" Nature 391: 288-291.

Jirholt et al., "Exploiting sequence space: shuffling in vivo formed complementarity determining regions into a master framework", *Gene*, 1998, 215:471-476.

Gibbs et al., "Degenerate oligonucleotide gene shuffling (DOGS): a method for enhancing the frequency of recombination with family shuffling", *Gene*, 2001, 271:13-20.

Rose et al., "Consensus-degenerate hybrid oligonucleotide primers for amplification of distantly related sequences", *Nucleic Acids Research*, 1998, 26(7):1628-1635.

International Search Report based on International Patent Application No. PCT/AU2001/001080 (Oct. 16, 2001).

* cited by examiner

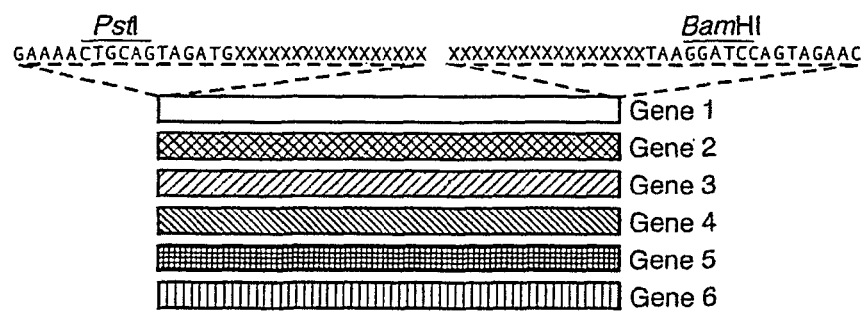

B.

Forward degenerate primer →

MQAAMTFTSNATGTYDGYYYELWKDTGNT.TMTVDTGGRF...
MQTSITLTSNASGTFDGYYYELWKDTGNT.TMTVYTQGRF...
MHAATIITNQTG.YDGVYYSFWIDGGGSVSMTLNGGGSY...
MAHARIITNNEMGNHSGYDYELWKDYGNT.SMTLNNGGAF...
MRADVVITSNQTGTHGGYNFEYWKDTGNG.TMVLKDGGAF...
MLAGRIIYDNETGTHGGYDYELWKDYGNT.IMELNDGGTF...

← Reverse degenerate primer

C.

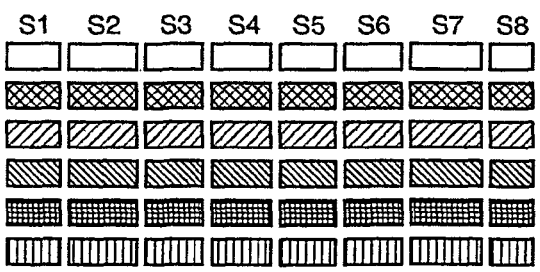

D.

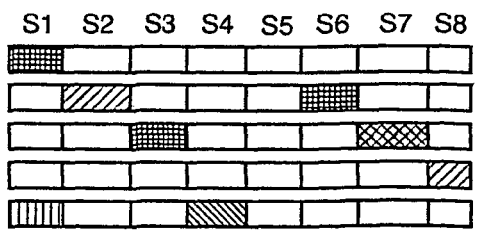

E. Screen individual genes for expression of desired phenotype

| | |
|---|---|
| D. thermophilum xynB | AGCAATATAAACAATGCATTATTCAGAACAGGTA |
| C. saccharolyticus Rt69B.1 xynD | AGTAACATTAACAATGCACTCTTCAGAACAGGTA |
| C. thermocellum xynV | AGCAATATCAACAATATTCTTTTCGTAAAGGTT |
| C. stercorarium xynA | AGTAATATGGTGCACTATTTAGAAAAGGGA |
| Bacillus sp. V1-4 xynA | AACAATATCGGAAATGCTTATTAGAAAAGGGA |
| S. roseiscleroticus xyl3 | ACCAACTGGGGCAACTTCGTCGCGCAAGGGCT |

B.

XINTF2 Forward CDE primer  5'- AAYATHRACAATGCATTATTCAGWAMAGG-3'
XINTR2 Reverse CDE primer  3'- TTRTADYTGTTACGTAATAAGTCWTKTCC-5'

Nondegenerate clamp

DEGENERATE OLIGONUCLEOTIDE GENE SHUFFLING

CROSS-REFERENCE TO RELATED APPLICATIONS

This application is a U.S. national stage application of International Application No. PCT/AU01/01080 filed Aug. 29, 2001 which claims priority from Australia Application Serial No. PQ9749 filed on Aug. 29, 2000.

TECHNICAL FIELD

The present invention relates to methods for gene shuffling to form mutant or chimeric genes encoding useful gene products.

BACKGROUND ART

Stemmer (Stemmer, W. P. C. Rapid evolution of a protein in vitro by DNA shuffling. *Nature* 370, 389-391, 1994; Stemmer, W. P. C. DNA shuffling by random fragmentation and reassembly: in vitro recombination for molecular evolution. *Proc. Natl. Acad. USA* 91, 10747-10751, 1994) has discussed the most effective methods to search sequence space in vitro to yield the greatest diversity of protein variants. Until recently, the most popular methods of creating combinatorial libraries are recursive strategies that seek to evolve sequences by the addition of point mutations. For in vitro evolution, inclusion of recombinant polymerase chain reaction PCR (gene shuffling) offers practical and theoretical advantages over simple recursive mutagenesis methods. It will rapidly fine tune the mutational load in several parts of the protein by recombining point mutations and wild-type sequences. The technique (and its variations) have been used to enhance enzyme activity, substrate specificity and stability. Family shuffling is usually achieved by fragmentation of the genes to be shuffled followed by PCR. This method relies on homologous recombination during the PCR reassembly step. Most methods require relatively high levels of sequence similarity between the genes to be shuffled as 'cross-over points' appear to occur in these regions.

If sequence similarity is low between the input genes, the majority products tend to be the reassembled parental genes and extensive searches need to be carried out to find recombinants (Kikuchi, M., Ohnishi, K. & Harayama, S. Novel family shuffling methods for the in vitro evolution of enzymes. Gene 236, 159-167, 1999; Qstermeier, M., Shim, J. H. & Benkovic, S. J. A combinatorial approach to hybrid enzymes independent of DNA homology. *Nat. Biotechnol.* 17, 1205-1209, 1999.). Kichuchi et al (1999) have reported on methods for gene shuffling that make use of unique restriction enzyme sites in the sequences of the parental molecules and following cleavage, several PCR steps were carried out to amplify the recombinant genes, a process that allowed hybrid genes to be formed at high frequency. An entirely different procedure was proposed by Ostermeier et al (1999) that allowed the preparation of combinatorial fusion libraries by progressive truncation of coding sequences of the two parental sequences followed by ligation of the fragments and selection for enzyme activity. Either parent can be used to provide 5' sequence for the hybrid gene. This procedure, termed iterative truncation for the creation of hybrid enzymes (ITCHY), can accommodate recombination between genes with as little as 50% sequence similarity and was found to give a wider range of crossovers compared with standard gene shuffling techniques.

The present inventors recently isolated a gene coding for a thermophilic beta-xylanase that had improved performance in the bleaching of paper pulp. It was desired to investigate the possibility of obtaining mutant derivatives that had enhanced stability and an altered pH optimum. Experiments using error-prone PCR and mis-incorporation mutagenesis followed by gene shuffling allowed the identification of mutant genes that coded for a limited sample of the variations in sequence space but required extensive screening for their identification. Gene shuffling following DNAseI fragmentation of related genes (family shuffling) overwhelmingly gave wild type parental sequences as the major products. After several trials of methods designed to reduce the background, a technique was devised that allows shuffling of genes that differ widely in sequence similarity and G:C content and greatly reduces the appearance of wild type genes. Furthermore, the primer extension conditions may be modified to bias the resulting progeny genes towards any one (or more) of the parental input genes. The present inventors term this procedure Degenerate Oligonucleotide Gene Shuffling (DOGS) and note its compatibility with other recursive point mutation techniques.

DISCLOSURE OF INVENTION

In a general first aspect, the present invention provides a method for gene shuffling to form a mutant or chimeric gene product, the method comprising:

(a) assigning one or more segments of the gene;

(b) amplifying the one or more of the assigned segments of the gene; and (c) causing recombination of the one or more amplified segments to form a mutant or chimeric gene.

In a second aspect, the present invention provides a method for forming a chimeric gene from two or more genes, the method comprising:

(a) assigning one or more segments of each gene;

(b) amplifying the one or more segments of the genes; and (c) combining at least some of the amplified segments so as to form a chimeric gene.

Preferably, the two or more genes belong to the same gene family encoding the same functional protein. It will be appreciated, however, that recombinant genes may be prepared from genes belonging to different families.

Preferably, the segments are assigned based on regions of encoded amino acid sequence of the gene. More preferably, the gene segments are assigned based on regions of conserved amino acid sequence of the respective gene product.

Preferably, the one or more assigned segments of the gene are amplified using primers specific for each segment.

Preferably, the amplifying of the one or more segments of the genes is achieved by using degenerate primers to produce amplified segments with complementary ends corresponding to the degenerate primers.

Preferably, the amplification is by polymerase chain reaction (PCR).

In one preferred form, the amplified segments are mixed in defined ratios so as to alter the likelihood of recombination of a segment into the chimeric gene. In this manner, a gene segment of interest can be provided in a higher ratio than other amplified segments to ensure that a higher percentage of recombinants will contain the segment of interest.

Preferably, the chimeric gene is produced by overlap extension of the combined amplified segments and multiple copies of the gene are produced by PCR amplification.

After the segments have been assigned in the gene(s) and the PCR primers specific for the gene segment devised, each segment is amplified, usually separately, from the parent gene(s) of interest. In order to obtain chimeric or mutant genes, the amplified segments are combined and joined by overlap extension. The mutant genes can then be placed in suitable expression vectors known to the art and the gene product produced. The resultant mutant gene product can be assayed for functional activity and compared with the activity of the parent gene product. Examples of possible gene products include, but not limited to, enzymes, growth factors, inhibitors, antibodies, antigens, structural proteins, transport proteins, toxins, and the like.

An advantage of the present invention is that there is no need to cleave the gene by nucleases prior to amplification and recombination. As a result, the present invention results in higher yields of chimera production and thus low generation of wild-type recombinants.

The gene(s) to be shuffled can be mutated or altered by standard techniques prior to being processed by the present invention.

In a third aspect, the present invention provides a chimeric or mutant gene produced by the method according to the first or second aspects of the present invention.

In a fourth aspect, the present invention provides an oligonucleotide primers having a non-degenerate core flanked by both 5' and 3' degenerate ends. These primers are referred to herein as complementary degenerate-end primers (CDE primers), in the amplification of segments of a gene to produce chimeric genes.

Preferably the oligonucleotide primer is suitable for use in gene shuffling and has a non-degenerate core based on a segment or template of a gene to be amplified and the core flanked by both 5' and 3' degenerate ends.

The 3' degenerate end gives each CDE primer their template-binding specificity, while the non-degenerate region acts as a stabilising clamp in subsequent rounds of the PCR. The 5' degenerate end is not required to contribute to the binding efficiency of the CDE primer during PCR, however, it plays an important role in allowing efficient binding and subsequent overlap-extension of PCR products (amplified gene segments) generated using respectively, the forward or the reverse CDE primers.

The non-degenerate core of CDE primers is generally based upon the corresponding coding sequence of one gene, designated the parental gene for shuffling. This results in the formation of chimeric fragments which retain parental sequence at the points of segment overlap.

CDE primers allow efficient and specific amplification of portions (referred to herein as gene segments) of related but divergent genes.

The 5' degenerate end of CDE primers ensures that separate PCR products generated with the respective forward or reverse complementary CDE primers can anneal equally well to initiate overlap extension, regardless of the parental origin of each segment.

The 3' and 5' degenerate ends of CDE primers would preferably be (though not limited to) 6-12 nucleotides in length, corresponding to 2-4 conserved amino acid residues. It will be appreciated that the length of the ends can vary depending on the gene or genes to be amplified.

The 3' and 5' degenerate ends of CDE primers should be of sufficient length to allow correct primer to template annealing in PCR amplification, or correct template to template annealing in overlap extension, and subsequent strand synthesis by a DNA polymerase.

Multiple (one or more) pairs of CDE primers allow the generation of consecutive PCR products (gene segments) with complementary ends suitable for overlap extension and PCR resulting in the generation of recombined segments.

CDE primers may also be used in combination with complementary degenerate primers that do not have a non-degenerate core to generate consecutive PCR products (gene segments) with complementary ends suitable for overlap extension and PCR resulting in the generation of recombined segments.

The mixing of segments amplified from related genes followed by overlap extension and PCR results in the efficient generation of chimeric gene fragments.

The non-degenerate core of each complementary CDE primer set may be (but does not have to be) based upon the gene designated the parental gene.

Gene segments amplified from related genes can be mixed in unequal amounts allowing control of the level of incorporation of each segment into resultant chimeric gene fragments.

In a fifth aspect, the present invention provides use of the primers according to the fourth aspect of the present invention to form mutant or chimeric genes.

In a sixth aspect, the present invention provides use of primers according to the fourth aspect of the present invention to incorporate mutations in genes. Preferably, degenerate 3' portions of the primers can allow point mutations to be incorporated into the final reassembled gene even though all segments are from the same parent.

Improvement of the biochemical characteristics of enzymes has been aided materially by random mutagenesis techniques involving misincorporation mutagenesis and DNA shuffling which have allowed exploration of the sequence space for selected proteins. The shuffling techniques can be used on a collection of mutants of the same parental gene or related families of proteins can be shuffled to produce multiple mutants with enhanced gene products. One difficulty with the current shuffling procedures is the predominance of unshuffled molecules in the pool of mutants. The present inventors have devised a procedure for gene shuffling based on consensus primers and PCR primer extension that allows control of the particular segments of a family of genes that are shuffled and reduces the frequency of the parental, non-recombinant products. This procedure has the advantage of avoiding the use of nucleases or restriction enzymes for gene fragmentation prior to shuffling and allows the use of random mutagenesis of selected segments of the gene as part of the procedure. The use of the technique has been successfully demonstrated with a diverse family of beta-xylanase genes of widely different G:C contents that provide a simple activity assay for identifying mutants.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the present invention may be more clearly understood, preferred forms will be described with reference to the following drawings and examples.

BRIEF DESCRIPTION OF DRAWINGS

FIG. 1. Overview of DOGS technique. A. Design oligonucleotide primers with 3' ends specific for the N- or C-terminus of each candidate gene, incorporate common nested 5' ends with suitable restriction sites for directional cloning of PCR products. PCR amplify each gene for use as PCT template. B. Design complementary degenerate-end primer pairs based upon one or more conserved motifs found in candidate genes. C. Amplify all of the individual segments for each gene (S1-S8) using the degenerate primers and the common nested primers. D. Mix segments from each gene to give desired levels of chimerisation. Polymerase-mediated overlap extension of segments to generate chimeric fragments. Regenerate full length genes by PCR with common nested primers. E. Digest and ligate full length chimeric gene fragments into a suitable vector, transform into *E. coli* and screen individual transformants for expression of protein with the desired phenotype.

FIG. 3. A. An alignment of related gene sequences. B. Complementary oligonucleotide sequences used for segment amplification from related genes, and for subsequent overlap extension. The non-degenerate core sequence (shown in reverse text) is designed to match the sequence of the selected parental gene (in the example below, *Dictyoglomus thermophilum* xynB).

MODES FOR CARRYING OUT THE INVENTION

Materials and Methods

PCR Concepts and Methodologies

Figure 2:
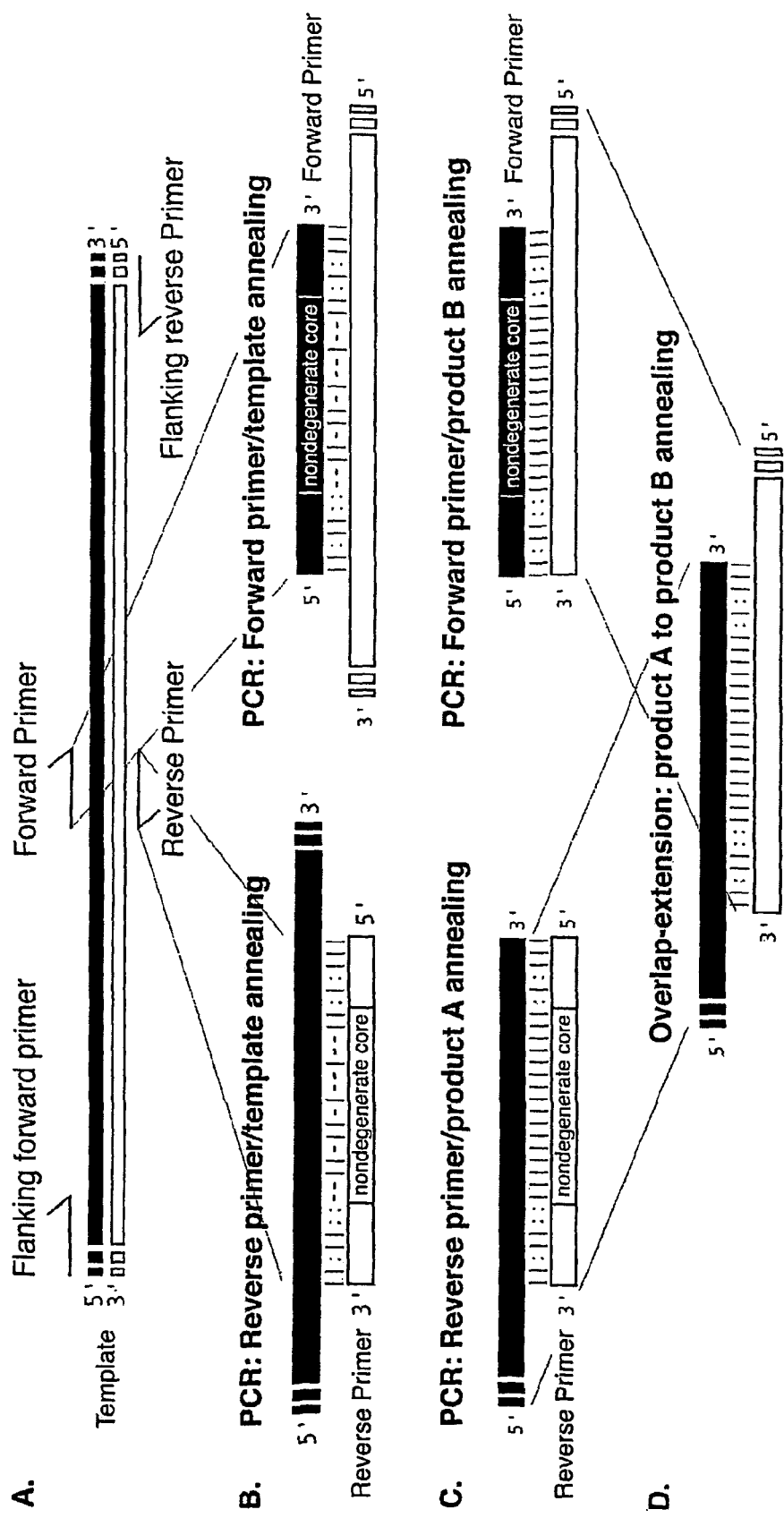
FIG. 2. Complementary degenerate-end primers for PCR and overlap-extension. A. A diagrammatic representation of double stranded template DNA and the relative binding positions of the complementary degenerate-end (CDE) forward and reverse primers. In separate PCR amplifications, the forward CDE primer is used combination with the reverse flanking primer, while the reverse CDE primer is used in combination with the forward flanking primer. B. A diagrammatic representation showing the correct binding of each of the CDE forward and reverse primers to the DNA template. A thin vertical line (|) indicates correct primer/template pairing of adjacent nucleotides; a colon (:) indicates potential matching of adjacent nucleotides due to degeneracy in the primer pool, while a dash (-) indicates a nucleotide mismatch. As depicted, in the first round of PCR amplification the non-degenerate core does not contribute to primer binding, and primer specificity is attained by the 3' degenerate end of each primer. C. A diagrammatic representation showing the binding of each of the CDE forward and reverse primers to product generated in early rounds of PCR amplification. A thin vertical line (|) indicates correct primer/template pairing of adjacent nucleotides; a colon (:) indicates potential matching of adjacent nucleotides due to degeneracy in the primer pool. As depicted, the non-degenerate core now acts as a clamp ensuring efficient utilisation of the degenerate primer pool in amplification of the correct target. D. A diagrammatic representation showing the complementarity of two PCR products generated using respectively, the forward or the reverse CDE primer. This complementarity allows for efficient polymerase-mediated overlap-extension resulting in the regeneration of a single DNA fragment comprised of both DNA regions. If the two PCR products have originated from different genes, a chimeric fragment will be generated.

PCR methods and theory can be found in a number of texts and references known to the art. The following reference: PCR Primer—A Laboratory Manual. 1995. Editors, Dieffenbach C. W. & Dveksler, G. S. Cold Spring Harbor Laboratory Press, USA, is a good example and is incorporated herein by reference.

Source of Genes

Family 11 xylanase genes were available from the following bacterial strains: *Dictyoglomus thermophilum* Rt46B.1 xynB (Morris, D. D. Gibbs, D. D., Chin, C. W., Koh, M. H., Wong, K. K. Y., Allison, R. W., Nelson, P. J. & Bergquist, P. L. Cloning of the xynB gene from *Dictyoglomus thermophilum* strain Rt46B.1 and action of the gene-product on kraft pulp. *Appl. Environ. Microbiol.* 64,1759-1765, 1998); *Clostridium stercorarium* xynB (Sakka, K., Kojima, Y., Kondo, T., Karita, S., Ohmiya, K. & Shimada, K. Nucleotide sequence of the *Clostridium stercorarium* xynA gene encoding xylanase A: identification of catalytic and cellulose binding domains. *Biosci. Biotechnol. Biochem.* 57, 273-277, 1993); *Bacillus* sp. V1-4 (Yang, V. W., Zhuang, Z., Elegir, G. & Jeffries, T. W. Alkaline-active xylanase produced by an alkaliphilic *Bacillus* sp isolated from kraft pulp. *J. Industrial Microbiol.* 15, 434-441, 1995); *Caldicellulosiruptor* sp. Rt69B.1 xynD (Morris, D. D., Gibbs, M. D., Ford, M., Thomas, J. & Bergquist, P. L. Family 10 and 11 xylanase genes from *Caldicellulosiruptor* isolate Rt69B.1. *Extremophiles* 3, 103-111, 1999); *Clostridium thermocellum* xynV (Fernandes A. C., Fontes C. M., Gilbert H. J., Hazlewood G. P., Fernandes T. H., Ferreira L. M. Homologous xylanases from *Clostridium thermocellum*: evidence for bi-functional activity, synergism between xylanase catalytic modules and the presence of xylan-binding domains in enzyme complexes. Biochem. J. 342, 105-110, 1999) and *Streptomyces roseiscleroticus* xyl3 (Elegir, G., Szakacs, G. & Jeffries, T. W. Purification, characterization and substrate specificity of multiple xylanases from *Streptomyces* sp strain B-12-2. *Appl. Environ. Microbiol.* 60, 2609-2615, 1994). Four of these xylanases were from thermophiles and coded for enzymes that had high temperature optima and the *Bacillus* and *Streptomyces* xylanase genes coded for mesophilic proteins that performed well in pulp bleaching tests.

Degenerate-end Complementary Primer Pairs for Efficient PCR Amplification of Gene Segments and Overlap-extension of Adjacent Segments The nucleotide sequences of the genes were aligned and degenerate consensus primers were designed based on the conserved amino acid motifs found in all of the genes. The genes coding for the xylanases could be divided into eight fragments on the basis of alignment of the conserved regions (see FIG. 4). Degenerate forward and reverse primers were designed which allowed amplification of the DNA in the eight segments when combined, as appropriate, with the nested 5' and 3'-common primers. Primer sequences are listed in Table 1.

deciding that this sequence should predominate in the shuffled progeny, the pooled PCR segments for each gene were mixed in the ration of 8.75 G1 to 1:1:1:1:1 to give chimeras with 5/8 segments from Rt46B.1 xynB. Fifty to 100 ng of mixed segments were then used as templates for overlap extension (Ho, S. N., Hunt, H. D., Horton, R. M., Pullen, J. K., & Pease, L. R. Site-directed mutagenesis by overlap extension using the polymerase chain reaction. *Gene* 77,

TABLE 1

Oligonucleotide primers used for gene isolation and gene segment amplification of xylanase genes from *Dictyoglomus thermophilum*[a]

Gene specific primers

```
DTF      (SEQ ID NO: 1)    5'-GAAAACTGCAGTAGATGCAAACGTCTATAACACT
DTR      (SEQ ID NO: 2)    5'-GTTCTACTGGATCCTTAAGAAAAAGTATTTTGTG
CSF      (SEQ ID NO: 3)    5'-GAAAACTGCAGTAGATGCTCGCCGGGCGAATAAT
CSR      (SEQ ID NO: 4)    5'-GTTCTACTGGATCCTTATCTGATTTCATTCTTGT
CTF      (SEQ ID NO: 5)    5'-GAAAACTGCAGTAGATGCGCGCTGATGTGGTAAT
CTR      (SEQ ID NO: 6)    5'-GTTCTACTGGATCCTTAGTTGCCAACAGTAATTG
BSF      (SEQ ID NO: 7)    5'-GAAAACTGCAGTAGATGGCCCATGCGAGAACCAT
BSR      (SEQ ID NO: 8)    5'-GTTCTACTGGATCCTTAGTTGCCAATAAACAGCT
RTF      (SEQ ID NO: 9)    5'-GAAAACTGCAGTAGATGCAGGCAGCCATGACATT
RTR      (SEQ ID NO: 10)   5'-GTTCTACTGGATCCTTAAGTAAATGTATTCTGTG
SRF      (SEQ ID NO: 11)   5'-GAAAACTGCAGTAGATGCACGCCGCCACTACCAT
SRR      (SEQ ID NO: 12)   5'-GTTCTACTGGATCCTTAACCGCTGACCGTGATGT
```

Nested Primers

```
SHF      (SEQ ID NO: 13)   5'-GAAAACTGCAGTAGATG
SHR      (SEQ ID NO: 14)   5'-GTTCTACTGGATCCTTA
```

Degenerate Primers

```
XINTF1C  (SEQ ID NO: 15)   5'-GGBTACDACTATGAACTATGGAARGA
XINTR1C  (SEQ ID NO: 16)   5'-TCYTTCCATAGTTCATAGTHGTAVCC
XINTF2C  (SEQ ID NO: 17)   5'-AAYATHRACAATGCATTATTCAGWAMAGG
XINTR2C  (SEQ ID NO: 18)   5'-CCTKTWCTGAATAATGCATTGTYDATRTT
XINTF3C  (SEQ ID NO: 19)   5'-GGNAAYTCCTATCTATGTATYTAYGG
XINTR3C  (SEQ ID NO: 20)   5'-CCRTARATACATAGATAGGARTTNCC
XINTF4B  (SEQ ID NO: 21)   5'-TGGGGHACCTGGCGTCCVMCNGG
XINTR4B  (SEQ ID NO: 22)   5'-CCNGKBGGACGCCAGGTDCCCCA
XINTF5   (SEQ ID NO: 23)   5'-ACCCGWGTWAATCAGCC
XINTR5   (SEQ ID NO: 24)   5'-GGCTGATTWACWCGGGT
XINTF6   (SEQ ID NO: 25)   5'-AARMGWACAAGYGGWAC
XINTR6   (SEQ ID NO: 26)   5'-GTWCCRCTTGTWCKYTT
XINTF7   (SEQ ID NO: 27)   5'-GAAGGWTAYCARAGCAG
XINTR7   (SEQ ID NO: 28)   5'-GTWCCRCTTGTWCKYTT
```

[a]IUB single letter code notation is used as follows; A, Adenosine; C, Cytidine; G, Guanine; T, Thymidine; R, G or A; Y, T or C; K, G or T; M, A or C; S, G or C; W, A or T; B, C G or T; D, A G or T; H, A C or T; V, A C or G; N, A C G or T.

In some cases, the degenerate oligonucleotides were designed using a modification of the CODEHOP method of Rose et al 1998 (Rose, T. M., Schultz, E. R., Henikoff, J. G., Pietrokovski, S. McCallum, C. M. & Henikoff, S. Consensus-degenerate hybrid oligonucleotide primers for amplification of distantly related sequences. *Nucleic Acids Res.* 26, 1628-1635, 1998). These primers consisted of a non-degenerate central core flanked by degenerate ends of 6-7 nucleotides. All of the segments for each gene were amplified with the consensus degenerate oligonucleotides and individually gel-purified from the PCR mixtures. PCR conditions for this step were: one cycle of 95° C. for 1 min.; then 35 cycles 95° C. (denaturation), 30 sec; annealing at 35° C., 20 sec; and extension at 72° C., 40 sec. with a final incubation at 72° C. for 5 min. using Life Technologies Platinum Pfx polymerase.

Overlap Extension

The segments of each gene after gel purification were mixed in the appropriate ratio to give the desired level of chimerisation. For example, using the six candidate genes G1-G6, where G1 is the *D. thermophilum* Rt46B.1 gene, and 51-59, 1989) using the following conditions: one cycle of 95° C. for 1 min; then 35 cycles 95° C. (denaturation), 30 sec; annealing at 35° C., 20 sec; and extension at 72° C., 40 sec. And a final incubation at 72° C. for 5 min using Life Technologies Platinum Pfx polymerase.

Chimera Amplification

Chimeric fragments were regenerated into complete genes by using the overlap-extended products (50-100 ng) as a template for PCR using the common flanking nested 5'- and 3'-primers under the following conditions: one cycle of 95° C. for 1 min. to activate the enzyme; then 20 cycles 95° C. (denaturation), 30 sec; annealing at 50° C., 20 sec; extension at 72° C., 40 sec. and a final incubation at 72° C. for 5 min using Life Technologies Inc Platinum Pfx DNA polymerase.

Cloning of Shuffled Products

DOGS PCR products were digested with the restriction enzymes BamHI and HindIII and ligated to pBSII KS- (Stratgene, Calif.) which had been digested with the same restriction enzymes, and treated with Shrimp alkaline phosphatase (Boehringer Mannheim). The ligated DNA was transformed into *E. Coli* strain DH5-alpha and plated onto plates containing ampicillin, X-gal and IPTG according to the vector manufacturers instructions. Individual colonies were picked and patched in duplicate onto new plates and screen for the expression of xylanase activity by the substrate overlay/Congo Red staining method as described in Morris et al 1999.

Enzyme Assays for Xylanase Activity

Methods for thermostability, pH optimum, etc, assays can be found in Morris et al 1999.

Results and Discussion

Rationale

An overview of the DOGS technique is given in FIG. 1. In FIG. 1A, Oligonucleotide primers are designed with 3' ends specific for the N- or C-terminus of each candidate gene, common nested 5' ends with suitable restriction sites for directional cloning PCR products are incorporated. Each gene is amplified for use as PCT template. In FIG. 1B, complementary degenerate-end primer pairs based upon one or more conserved motifs found in candidate gene are designed. In FIG. 1C, all of the individual segments for each gene are amplified using the degenerate primers and the common nested primers. In FIG. 1D, segments from each gene are mixed to give desired levels of chimerisation. Polymerase-mediated overlap extension of segments is used to generate chimeric fragments and full length genes are generated by PCR with common nested primers. In FIG. 1E, full length fragments are digested and ligated into cloning vector, transformed into *E. coli* and individual recombinants screened for desired properties.

Complementary degenerate-end primers for PCR and overlap-extension are shown in FIG. 2. FIG. 2A depicts a diagrammatic representation of double stranded template DNA and the relative binding positions of the complementary degenerate-end (CDE) forward and reverse primers. In separate PCR amplifications, the forward CDE primer is used combination with the reverse flanking primer, while the reverse CDE primer is used in combination with the forward flanking primer. FIG. 2B depicts a diagrammatic representation showing the correct binding of each of the CDE forward and reverse primers to the DNA template. A thin vertical line (|) indicates correct primer/template pairing of adjacent nucleotides; a colon (:) indicates potential matching o adjacent nucleotides due to degeneracy in the primer pool, while a dash (-) indicates a nucleotide mismatch. As depicted, in the first round of PCR the non-degenerate core does not contribute to primer binding, and primer specificity is attained by the 3' degenerate end of each primer. FIG. 2C depicts a diagrammatic representation showing the binding of each of the CDE forward and reverse primers to product generated in early rounds of PCR amplification. A thin vertical line (|) indicates correct primer/template pairing of adjacent nucleotides; a colon (:) indicates potential matching of adjacent nucleotides due to degeneracy in the primer pool. As depicted, the non-degenerate core now acts as a clamp ensuring efficient utilisation of the degenerate primer pool in amplification of the correct target. FIG. 2D depicts a diagrammatic representation showing the complementarity of two PCR products generated using respectively, the forward or the reverse CDE primer. This complementarity allows for efficient polymerase-mediated overlap-extension resulting in the regeneration of a single DNA fragment comprised of both DNA regions. If the two PCR products have originated from different genes, a chimeric fragment will be generated.

This procedure was developed after finding a high frequency of parental non-shuffled products in early experiments using the established technique with DNAseI fragmentation introduced by Stemmer (1994a). This observation made extensive screening necessary for the isolation of candidate chimeric genes, particularly when distantly related genes are used in family shuffling. The background of parental molecules may also have been a consequence of the difficulty of completely removing undigested, full-length material during the gel purification of the fragments. The restriction enzyme approach by Kikuchi et al (1999) has the merits of simplicity and the wide range of restriction enzymes available should lower the frequency of regeneration of wild-type genes. In use, however, the method does not obtain the desired number or frequency of altered gene products. It was considered that it may be important to control the input of parental genes into the shuffling procedure and the present inventors demonstrated the rarity with which chimeras arose when genes with limited sequence similarity were used as parents. A description of the products from experiments entailing shuffling the six xylanase genes, using xynB from Rt46B.1 as the major input DNA is described below.

Degenerate-end Complementary Primer Pairs for Efficient PCR Amplification of Gene Segments and Overlap-extension of Adjacent Segments The most commonly used strategy to isolate distantly-related sequences by PCR has been to design degenerate primers which bind to highly conserved regions of DNA sequence. The difficulty with this method is that as the primer degeneracy increases to accommodate more divergent genes, the number of primer molecules in a PCR that can correctly prime synthesis drops, and these primers may be used up in the first few cycles of the reaction. Non-specific amplification may then occur because of the abundance of primers that do not participate in amplification of the targeted gene, and so are available to prime non-specific synthesis, especially as low stringency annealing conditions are usually needed to detect mismatched homologs.

Rose et al. (1998) have described a strategy that overcomes problems of degenerate methods for primer design called Consensus-Degenerate Hybrid Oligonucleotide Primers (CODEHOP). CODEHOP primers consist of a relatively short 3' degenerate end and a 5' non-degenerate consensus clamp. Reducing the length of the 3' core to a minimum decreases the total number of individual primers in the degenerate primer pool. Hybridization of the 3' degenerate end with the target template is stabilized by the 5' non-degenerate consensus clamp, which allows higher annealing temperatures without increasing the degeneracy of the pool. Although potential mismatches may occur between the 5' consensus clamp of the primer and the target sequence during the initial PCR cycles, they are situated away from the 3' hydroxyl extension site, and so mismatches between the primer and the target are less disruptive to priming of polymerase extension. Further amplification of primed PCR products during subsequent rounds of primer hybridization and extension is enhanced by the sequence similarity of all primers in the pool; this potentially allows utilization of all primers in the reaction.

A modification of the CODEHOP oligonucleotide design technique described and utilised by the present inventors allows efficient amplification of multiple overlapping segments of related genes, and subsequent overlap-extension of adjacent segments from different genes resulting in the formation of useful chimeric gene fragments or products.

The new technique entails the design of complementary pairs of primers. Each primer has a non-degenerate core flanked by both 5' and 3' degenerate ends, referred to herein as complementary degenerate-end primers (CDE primers). As with the CODEHOP primers, the 3' degenerate end gives each CDE primer its template-binding specificity, while the non-degenerate region acts as a stabilising clamp in subsequent rounds of the PCR amplification. The 5' degenerate end is not required to contribute to the binding efficiency of the CDE primer during PCR, however, it plays an important role in allowing efficient binding and subsequent overlap-extension of PCR products (gene segments) generated using respectively, the forward or the reverse CDE primers.

The non-degenerate core of CDE primers is generally based upon the corresponding coding sequence of one gene, designated the parental gene for shuffling. This results in the formation of chimeric fragments which retain parental sequence at the points of segment overlap. An example of the design strategy for making complementary oligonucleotide pairs suitable for the amplification of gene segments from related genes, and for the subsequent overlap extension of segments to generate chimeric genes, is shown in FIG. 3.

Shuffling with *D. thermophilum* Rt46B.1 xynB as the Major Parent

Three gene shuffling libraries were generated, each with differing ratios of input DNAs. Libraries R1, R2 and R3 were generated by mixing equal amounts of each of the major parent gene segments with other gene segments in the ratios shown in Table 2. The ratios used were calculated to give on average 5/8, 6/8 and 7/8 major parent segments per gene, for the respective R1, R2 and R3 libraries.

introduction of point mutations introduced by the degeneracy in the primers used to amplify each segment. Also, in 6 of the 30 xylanase-negative isolates, frameshifts were observed at a segment boundary, presumably introduced during the overlap extension of adjacent segments and resulted in truncated open reading frames in all cases observed.

Figure 4:
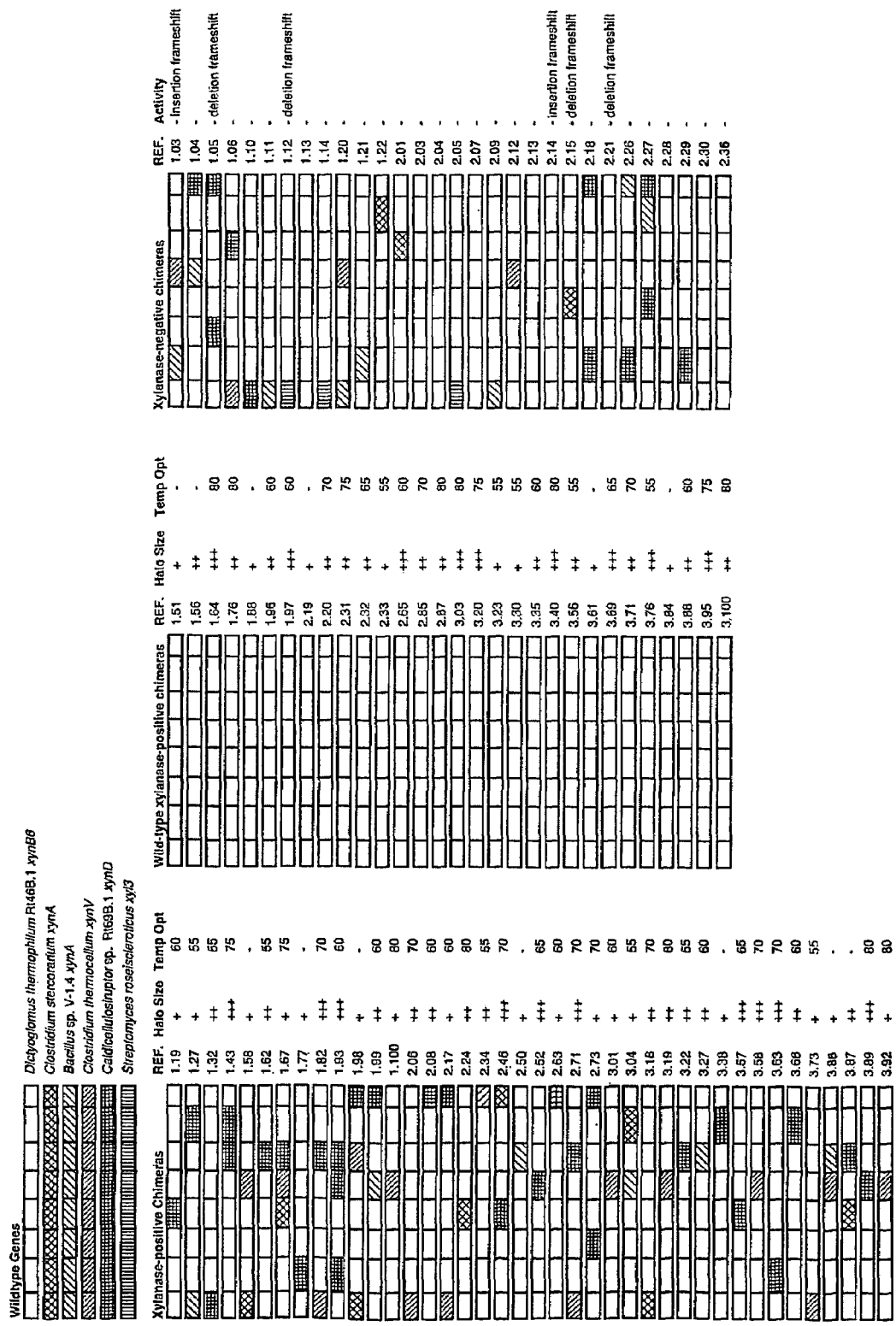
FIG. 4. Experiment R—shuffling results with *D. thermophilum* as the major parent.

What is striking about FIG. 4, as detailed in Table 2, is that 52-75% of the recombinant genes were chimeric. The preponderance of Rt46B.1 xynB segments were close to what would be expected from the input ratios. Some wild-type isolates were inactive in the plate test for xylanase activity but this result can be explained by the introduction of point mutations at the segment overlap boundaries due to the degenerate regions contained within the primers.

A further experiment was carried out in which the output ratios for all segments were 1:1:1:1:1:1. A total of 20 chimeras were sequenced and on average only one segment per chimera was derived from *D. thermophilum* xynB6. This result indicated that the xynB6-derived degenerate clamp of CDE primers did not bias recombination toward reformation of the parental gene.

Xylanase Assays on Shuffled Gene Products

Figure 5:
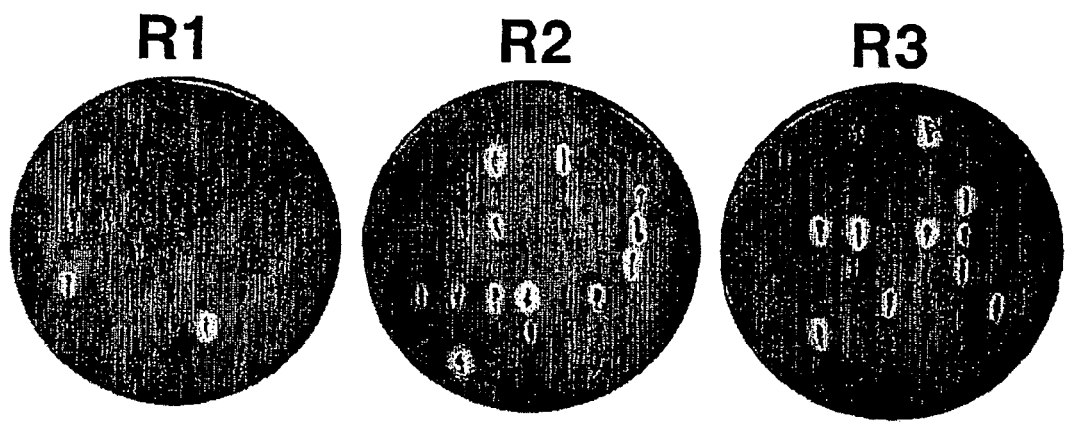
FIG. 5. Representation of individual colonies patched to plates, overlayed with 0.5% xylan and stained with Congo Red to reveal expression of xylanase activity. An unstained region surrounding a colony indicates enzymatic digestion of the xylan.
Figure 6:
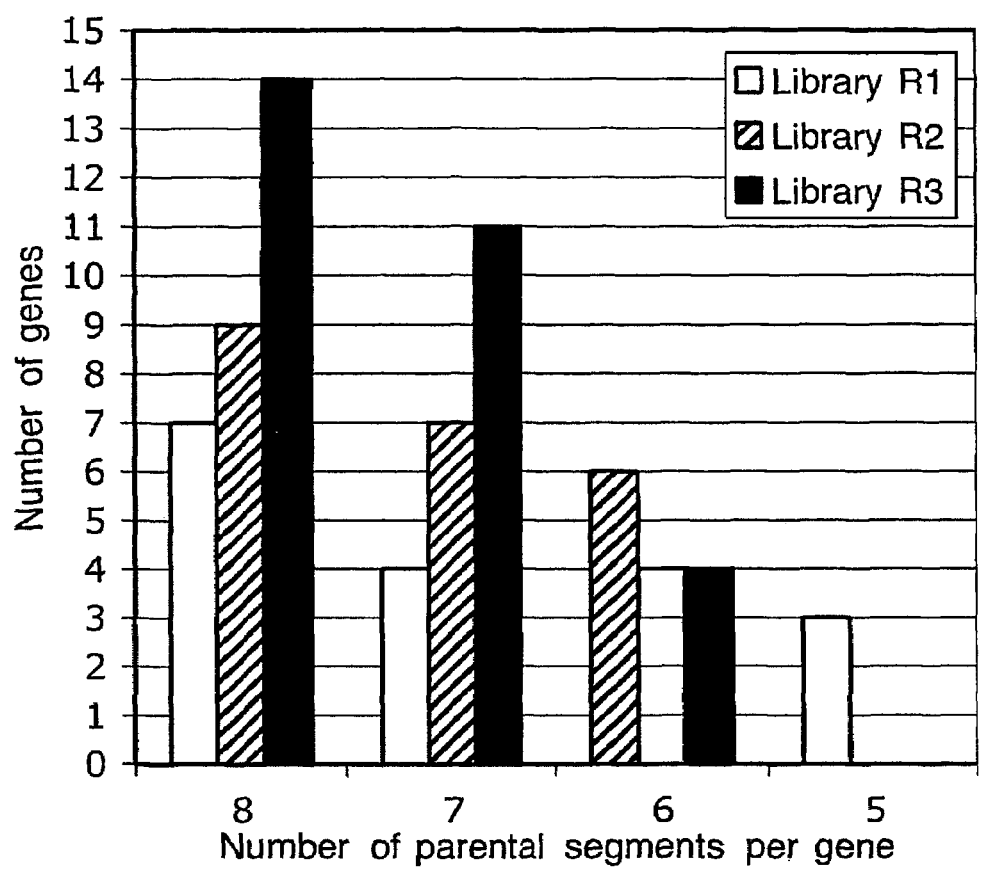
FIG. 6. Graph showing relative frequency of segment shuffling with differing ratios of input segments. The libraries R1, R2 and R3 were generated by mixing parental gene segments with other gene segments at a ratio of 8.75:1:1:1:1:1, 15:1:1:1:1:1 and 35:1:1:1:1:1 respectively.

Results of gene shuffling experiments of xylanase genes are shown in FIGS. 5 and 6. A large number of active chimeric genes was produced by the method according to the present invention.

The Use of Nested Primer Sets for Gene Shuffling and Misincorporation Mutagenesis In the method described, gene-specific primer sets (forward and reverse) with gene-specific 3' ends and common

TABLE 2

Observed levels of chimerisation in DOGS gene shuffling libraries

| Library | Input ratio[a] | Predicted chimera frequency[b] | Xylanase phenotype | Plasmid inserts with observed major parent segments per gene | | | | Total genes | Observed chimerism[c] | Percentage chimeric genes |
|---|---|---|---|---|---|---|---|---|---|---|
| | | | | 8/8 | 7/8 | 6/8 | 5/8 | | | |
| R1 | 8.75:1:1:1:1:1 | 5/8 | + | 7 | 4 | 6 | 3 | 20 | 6.72/8 | 75 |
| | | | − | 1 | 6 | 5 | 0 | 12 | | |
| R2 | 15:1:1:1:1:1 | 6/8 | + | 8 | 7 | 4 | 0 | 19 | 7.24/8 | 54 |
| | | | − | 9 | 6 | 2 | 1 | 18 | | |
| R3 | 35:1:1:1:1:1 | 7/8 | + | 15 | 13 | 3 | 0 | 31 | 7.39/8 | 52 |
| | | | − | nd[d] | nd | nd | nd | — | | |

Figure 7:
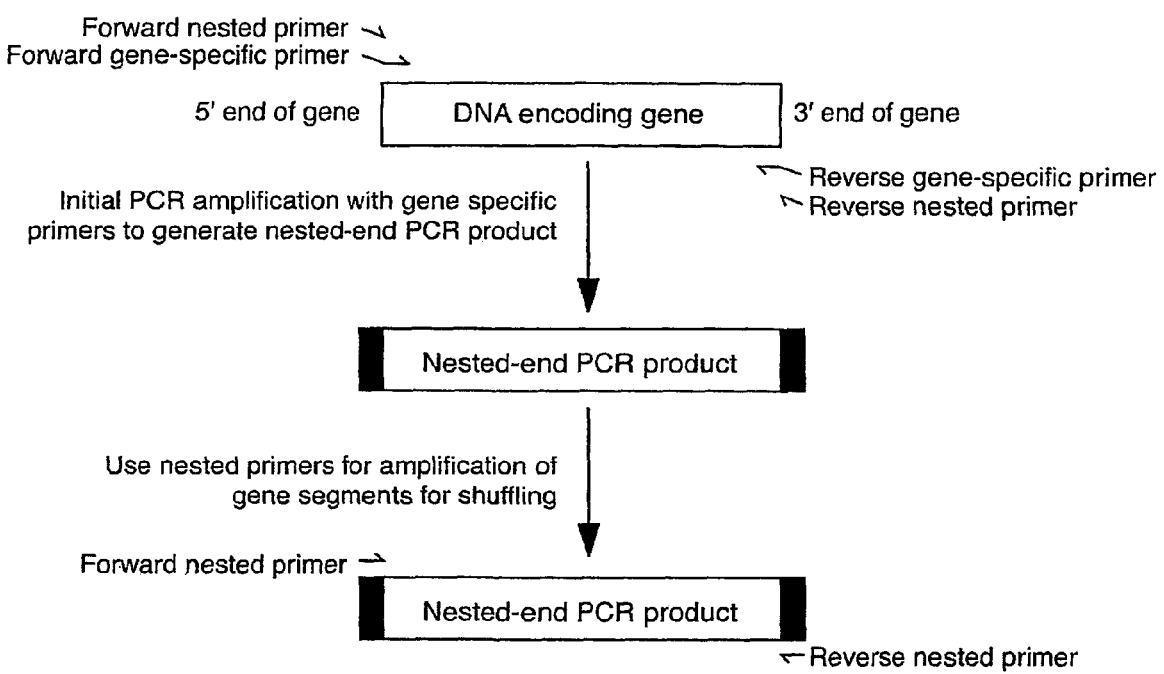
FIG. 7. A diagram illustrating the relative binding positions and use of nested primer sets to incorporate common nested ends onto genes for use in subsequent PCR amplification of gene segments for gene shuffling.

[a]Ratio of amount of major parent (*D. thermophilum xynB*) DNA to DNA from other genes
[b]Predicted average number of major parent segments out of 8 segments per xylanase gene
[c]Observed average number of major parent segments out of 8 segments per xylanase gene
[d]nd, not determined A total of 100 colonies from each library were screened for the expression of xylanase activity. Seventy xylanase-positive transformants and 30 xylanase-negative transformants were identified and the plasmid insert of each was sequenced and the resulting data compared to the parental sequences. It was possible to assign the origin of each segment in a recombinant from the sequence data, as shown in FIG. 4. Of the 100 genes sequenced, 75% were chimeric for library R1, while 54% and 52% were chimeric for libraries R2 and R3 respectively. The xylanase-positive chimeras are shown in FIG. 4. With these input ratios, a dominance of parental Rt46B.1 xynB sequences from the input ratios was expected. Some isolates that contained all parental Rt46B.1 segments were inactive in the plate test. These results can be explained by the 5'-overhanging ends were designed for the genes selected for DNA shuffling. Forward and reverse nested primers were designed to be substantially identical to the 5'-overhanging ends of the gene-specific primers. Each gene was initially PCR amplified using the gene-specific primer sets. Each PCR product could then be used in subsequent PCR amplification using the common nested primer set, or for amplification of individual gene segments (see FIG. 7).

The use of nested primers assists in ensuring that the end (5' and 3') segments of genes can be amplified, and that following overlap extension PCR, chimeric genes can be amplified equally well regardless of which genes contributed to the end (5' and 3') segments.

The use of nested primers assists in ensuring that any mis-incorporation mutagenesis procedure is capable of changing possible codons within the gene to be mutated.

CONCLUSIONS

The DOGS procedure described above demonstrates that it is possible to shuffle members of a gene family that are not particularly closely related and still obtain chimeric molecules at high frequency so that comprehensive and time consuming screens are not necessary, in comparison with prior art methods. The recombination frequencies can be controlled by altering the segment input ratios so that shuffling of particular fragments can be enhanced. Accordingly, the procedure allows domain-swapping experiments to be conducted with relative ease, replacing previous methods relying on suitable restriction enzyme sites. It is evident that PCR-induced misincorporation or error-prone mutagenesis can be incorporated as part of the procedure to introduce even more diversity into the products. In this respect, it lends itself to random mutagenesis of individual segments to assist in fine-tuning of the encoded enzyme product. It gives the investigator control over the extent and nature of specific segment mutagenesis by introducing a DNA polymerase without proof-reading activity at an appropriate step in the procedure. In addition, it is clear from the design of the degenerate primers and the results that altered nucleotide sequences will be generated even using a high fidelity DNA polymerase because of the mismatches inherent in the primers. Even greater mis-incorporation mutagenesis can be generated by employing a polymerase without proof-reading activity in the amplification and primer extension steps.

The use of CDE primers has allowed the reliable PCR amplification and shuffling of equivalent gene segments from a diverse range of genes with low overall sequence homology. The CDE primers used ranged from 23-29 nucleotides in length. The CDE primers used in this study represent may not represent the maximum degree of degeneracy tolerated in order for segment amplification and subsequent overlap extension to work reliably. Accordingly, the length of the primers can vary depending on the source of the parent gene or genes and the segments to be amplified.

The experiments described above have used only a single round of chimera formation. Clearly, more diversity can be introduced to allow exploration of the sequence space by additional rounds of DOGS. The procedure lends itself to combination with other gene shuffling and combinatorial mutagenesis techniques.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for gene shuffling to form at least one mutant or chimeric gene, the method comprising:
amplifying at least a first segment of a first parental gene and a second segment of a second parental gene, wherein at least one first segment is amplified using a first primer comprising a non-degenerate core flanked by 5' and 3' degenerate ends, and wherein at least one second segment is amplified using a second primer comprising a non-degenerate core flanked by 5' and 3' degenerate ends, wherein the non-degenerate core of the first primer is complementary to the non-degenerate core of the second primer; and
causing recombination between at least one amplified first segment and at least one amplified second segment to form at least one mutant or chimeric gene.

2. The method according to claim 1 wherein the recombination forms two or more mutant or chimeric genes.

3. The method according to claim 1 or 2 wherein the parental genes belong to the same gene family encoding proteins having the same function.

4. The method according to claim 1 or 2 wherein the parental genes belong to different gene families encoding proteins with different functions.

5. The method according to claim 1 or 2 wherein the gene segments are selected based on regions of conserved amino acid sequence of the respective gene products encoded by the parental genes.

6. The method according to claim 1 or 2 wherein the amplification is by polymerase chain reaction (PCR).

7. The method according to claim 1 or 2 wherein the amplified segments are mixed in substantially equal ratios for the recombination.

8. The method according to claim 1 or 2 wherein at least one mutant or chimeric gene is produced by overlap extension of the combined amplified segments and multiple copies of the mutant or chimeric gene are produced by PCR amplification.

9. The method according to claim 1 or 2 wherein at least one mutant or chimeric gene is placed in suitable expression vector and the gene product is produced from the mutant or chimeric gene.

10. The method according to claim 1 or 2 wherein at least one mutant or chimeric gene encodes a protein selected from the group consisting of enzyme, growth factor, inhibitor, antibody, antigen, structural protein, transport protein, toxin, and combination thereof.

11. The method according to claim 1 or 2 wherein at least one mutant or chimeric gene is further mutated or altered.

12. The method according to claim 1 or 2, wherein the non-degenerate cores flanked by both 5' and 3' degenerate ends of the primers act as a stabilizing clamp.

13. The method according to claim 1 or 2 wherein the 3' degenerate ends of the primers give the primers template-binding specificity.

14. The method according to claim 1 or 2 wherein subsequent rounds of amplification are performed, wherein the non-degenerate cores of the primers act as a stabilizing clamp.

15. The method according to claim 1 or 2 wherein the amplified gene segments are subjected to overlap-extension amplification, wherein the portions of amplified gene segments derived from the 5' degenerate ends of the primers allow for efficient binding and overlap-extension.

16. The method according to claim 1 or 2 wherein the non-degenerate cores of the primers are based upon the corresponding coding sequence of at least one parental gene.

17. The method according to claim 1 or 2 wherein the non-degenerate core of the primers has 11 nucleotides.

18. The method according to claim 1 or 2 wherein the non-degenerate core of the primers has from 5 to 16 nucleotides.

19. The method according to claim 1 or 2 wherein the non-degenerate core of the primers has 16 nucleotides.

20. The method according to claim 1 or 2 wherein the non-degenerate core of the primers has 5 nucleotides.

21. The method according to claim 1 or 2 wherein multiple mutant or chimeric genes are produced and wherein the multiple mutant or chimeric genes are further mutated or altered.

* * * * *

```
                        SEQUENCE LISTING

<160> NUMBER OF SEQ ID NOS: 28

<210> SEQ ID NO 1
<211> LENGTH: 34
<212> TYPE: DNA
<213> ORGANISM: Dictyoglomus thermophilum

<400> SEQUENCE: 1
gaaaactgca gtagatgcaa acgtctataa cact                              34

<210> SEQ ID NO 2
<211> LENGTH: 34
<212> TYPE: DNA
<213> ORGANISM: Dictyoglomus thermophilum

<400> SEQUENCE: 2
gttctactgg atccttaaga aaaagtattt tgtg                              34

<210> SEQ ID NO 3
<211> LENGTH: 34
<212> TYPE: DNA
<213> ORGANISM: Dictyoglomus thermophilum

<400> SEQUENCE: 3
gaaaactgca gtagatgctc gccgggcgaa taat                              34

<210> SEQ ID NO 4
<211> LENGTH: 34
<212> TYPE: DNA
<213> ORGANISM: Dictyoglomus thermophilum

<400> SEQUENCE: 4
gttctactgg atccttatct gatttcattc ttgt                              34
```

```
<210> SEQ ID NO 5
<211> LENGTH: 34
<212> TYPE: DNA
<213> ORGANISM: Dictyoglomus thermophilum

<400> SEQUENCE: 5
gaaaactgca gtagatgcgc gctgatgtgg taat                              34

<210> SEQ ID NO 6
<211> LENGTH: 34
<212> TYPE: DNA
<213> ORGANISM: Dictyoglomus thermophilum

<400> SEQUENCE: 6
gttctactgg atccttagtt gccaacagta attg                              34

<210> SEQ ID NO 7
<211> LENGTH: 34
<212> TYPE: DNA
<213> ORGANISM: Dictyoglomus thermophilum

<400> SEQUENCE: 7
gaaaactgca gtagatggcc catgcgagaa ccat                              34

<210> SEQ ID NO 8
<211> LENGTH: 34
<212> TYPE: DNA
<213> ORGANISM: Dictyoglomus thermophilum

<400> SEQUENCE: 8
gttctactgg atccttagtt gccaataaac agct                              34

<210> SEQ ID NO 9
<211> LENGTH: 34
<212> TYPE: DNA
<213> ORGANISM: Dictyoglomus thermophilum

<400> SEQUENCE: 9
gaaaactgca gtagatgcag gcagccatga catt                              34

<210> SEQ ID NO 10
<211> LENGTH: 34
<212> TYPE: DNA
<213> ORGANISM: Dictyoglomus thermophilum

<400> SEQUENCE: 10
gttctactgg atccttaagt aaatgtattc tgtg                              34

<210> SEQ ID NO 11
<211> LENGTH: 34
<212> TYPE: DNA
<213> ORGANISM: Dictyoglomus thermophilum

<400> SEQUENCE: 11
gaaaactgca gtagatgcac gccgccacta ccat                              34

<210> SEQ ID NO 12
<211> LENGTH: 34
<212> TYPE: DNA
<213> ORGANISM: Dictyoglomus thermophilum

<400> SEQUENCE: 12
gttctactgg atccttaacc gctgaccgtg atgt                              34
```

<210> SEQ ID NO 13
<211> LENGTH: 17
<212> TYPE: DNA
<213> ORGANISM: Dictyoglomus thermophilum

<400> SEQUENCE: 13
gaaaactgca gtagatg 17

<210> SEQ ID NO 14
<211> LENGTH: 17
<212> TYPE: DNA
<213> ORGANISM: Dictyoglomus thermophilum

<400> SEQUENCE: 14
gttctactgg atcctta 17

<210> SEQ ID NO 15
<211> LENGTH: 26
<212> TYPE: DNA
<213> ORGANISM: Artificial Sequence
<220> FEATURE:
<221> NAME/KEY: misc_feature
<222> LOCATION: (3)..(25)
<223> OTHER INFORMATION: b = c or g or t; d = a or g or t; r = a or g.
<220> FEATURE:
<223> OTHER INFORMATION: Description of Artificial Sequence: degenerate
      primer

<400> SEQUENCE: 15
ggbtacdact atgaactatg gaarga 26

<210> SEQ ID NO 16
<211> LENGTH: 26
<212> TYPE: DNA
<213> ORGANISM: Artificial Sequence
<220> FEATURE:
<221> NAME/KEY: misc_feature
<222> LOCATION: (3)..(24)
<223> OTHER INFORMATION: y = c or t; h = a, c or t; v = a or c or g.
<220> FEATURE:
<223> OTHER INFORMATION: Description of Artificial Sequence: degenerate
      primer

<400> SEQUENCE: 16
tcyttccata gttcatagth gtavcc 26

<210> SEQ ID NO 17
<211> LENGTH: 29
<212> TYPE: DNA
<213> ORGANISM: Artificial Sequence
<220> FEATURE:
<221> NAME/KEY: misc_feature
<222> LOCATION: (3)..(26)
<223> OTHER INFORMATION: y = c or t; r = a or g; w = a or t; m = a or c.
<220> FEATURE:
<223> OTHER INFORMATION: Description of Artificial Sequence: degenerate
      primer

<400> SEQUENCE: 17
aayathraca atgcattatt cagwamagg 29

<210> SEQ ID NO 18
<211> LENGTH: 29
<212> TYPE: DNA
<213> ORGANISM: Artificial Sequence
<220> FEATURE:
<221> NAME/KEY: misc_feature
<222> LOCATION: (4)..(27)
<223> OTHER INFORMATION: k = g or t; w = a or t; y = c or t; d = a or g
      or t; r = a or g.
<220> FEATURE:
<223> OTHER INFORMATION: Description of Artificial Sequence:  degenerate
      primer

<400> SEQUENCE: 18
cctktwctga ataatgcatt gtydatrtt                                    29

<210> SEQ ID NO 19
<211> LENGTH: 26
<212> TYPE: DNA
<213> ORGANISM: Artificial Sequence
<220> FEATURE:
<221> NAME/KEY: misc_feature
<222> LOCATION: (3)..(24)
<223> OTHER INFORMATION: n = a, c, g or t; y = c or t.
<220> FEATURE:
<223> OTHER INFORMATION: Description of Artificial Sequence:  degenerate
      primer

<400> SEQUENCE: 19
ggnaaytcct atctatgtat ytaygg                                       26

<210> SEQ ID NO 20
<211> LENGTH: 26
<212> TYPE: DNA
<213> ORGANISM: Artificial Sequence
<220> FEATURE:
<221> NAME/KEY: misc_feature
<222> LOCATION: (3)..(24)
<223> OTHER INFORMATION: r = a or g; n = a, c, g or t.
<220> FEATURE:
<223> OTHER INFORMATION: Description of Artificial Sequence:  degenerate
      primer

<400> SEQUENCE: 20
ccrtaratac atagatagga rttncc                                       26

<210> SEQ ID NO 21
<211> LENGTH: 23
<212> TYPE: DNA
<213> ORGANISM: Artificial Sequence
<220> FEATURE:
<221> NAME/KEY: misc_feature
<222> LOCATION: (6)..(21)
<223> OTHER INFORMATION: h = a, c or t; v = a, c or g; m = a or c;
      n = a, c, g or t.
<220> FEATURE:
<223> OTHER INFORMATION: Description of Artificial Sequence:  degenerate
      primer

<400> SEQUENCE: 21
tgggghacct ggcgtccvmc ngg                                          23

<210> SEQ ID NO 22
<211> LENGTH: 23
<212> TYPE: DNA
<213> ORGANISM: Artificial Sequence
<220> FEATURE:
<221> NAME/KEY: misc_feature
<222> LOCATION: (3)..(18)
<223> OTHER INFORMATION: n = a, c, g or t; k = g or t; b = c or g or t;
      d = a or g or t.
<220> FEATURE:
<223> OTHER INFORMATION: Description of Artificial Sequence:  degenerate
      primer

<400> SEQUENCE: 22

-continued ccngkbggac gccaggtdcc cca                                         23

<210> SEQ ID NO 23
<211> LENGTH: 17
<212> TYPE: DNA
<213> ORGANISM: Artificial Sequence
<220> FEATURE:
<221> NAME/KEY: misc_feature
<222> LOCATION: (6)..(9)
<223> OTHER INFORMATION: w = a or t.
<220> FEATURE:
<223> OTHER INFORMATION: Description of Artificial Sequence: degenerate
      primer

<400> SEQUENCE: 23
acccgwgtwa atcagcc                                                17

<210> SEQ ID NO 24
<211> LENGTH: 17
<212> TYPE: DNA
<213> ORGANISM: Artificial Sequence
<220> FEATURE:
<221> NAME/KEY: misc_feature
<222> LOCATION: (9)..(12)
<223> OTHER INFORMATION: w = a or t.
<220> FEATURE:
<223> OTHER INFORMATION: Description of Artificial Sequence: degenerate
      primer

<400> SEQUENCE: 24
ggctgattwa cwcgggt                                                17

<210> SEQ ID NO 25
<211> LENGTH: 17
<212> TYPE: DNA
<213> ORGANISM: Artificial Sequence
<220> FEATURE:
<221> NAME/KEY: misc_feature
<222> LOCATION: (4)..(15)
<223> OTHER INFORMATION: m = a or c; w = a or t; y = c or t.
<220> FEATURE:
<223> OTHER INFORMATION: Description of Artificial Sequence: degenerate
      primer

<400> SEQUENCE: 25
aarmgwacaa gyggwac                                                17

<210> SEQ ID NO 26
<211> LENGTH: 17
<212> TYPE: DNA
<213> ORGANISM: Artificial Sequence
<220> FEATURE:
<221> NAME/KEY: misc_feature
<222> LOCATION: (3)..(15)
<223> OTHER INFORMATION: w = a or t; r = a or g; k = g or t; y = c or t.
<220> FEATURE:
<223> OTHER INFORMATION: Description of Artificial Sequence: degenerate
      primer

<400> SEQUENCE: 26
gtwccrcttg twckytt                                                17

<210> SEQ ID NO 27
<211> LENGTH: 17
<212> TYPE: DNA
<213> ORGANISM: Artificial Sequence
<220> FEATURE:
<221> NAME/KEY: misc_feature
<222> LOCATION: (6)..(12)
<223> OTHER INFORMATION: w = a or t; y = c or t; r = a or g.

-continued

```
<220> FEATURE:
<223> OTHER INFORMATION: Description of Artificial Sequence:  degenerate
      primer

<400> SEQUENCE: 27
gaaggwtayc aragcag                                                    17

<210> SEQ ID NO 28
<211> LENGTH: 17
<212> TYPE: DNA
<213> ORGANISM: Artificial Sequence
<220> FEATURE:
<221> NAME/KEY: misc_feature
<222> LOCATION: (3)..(15)
<223> OTHER INFORMATION: w = a or t; r = a or g; k = g or t; y = c or t;
<220> FEATURE:
<223> OTHER INFORMATION: Description of Artificial Sequence:  degenerate
      primer

<400> SEQUENCE: 28
gtwccrcttg twckytt                                                    17
```